United States Patent [19]

Quinlan

[11] 4,352,891
[45] Oct. 5, 1982

[54] DIETHYLCARBAMAZINE RESINATE AND STYRLPYRIDINIUM RESINATE-DIETHYLCARBAMAZINE RESINATE EDIBLE ANTHELMINTIC TABLETS FOR COMPANION ANIMALS

[75] Inventor: James M. Quinlan, Trenton, N.J.

[73] Assignee: American Cyanamid Co., Stamford, Conn.

[21] Appl. No.: 196,242

[22] Filed: Oct. 14, 1980

Related U.S. Application Data

[63] Continuation-in-part of Ser. No. 74,211, Sep. 10, 1979, abandoned.

[51] Int. Cl.³ .................... B01J 41/12; A61K 31/495
[52] U.S. Cl. .................................... 521/32; 424/250; 542/455; 544/390
[58] Field of Search ............... 424/250; 542/455, 471; 544/386, 390; 521/32

[56] References Cited
FOREIGN PATENT DOCUMENTS 946742  5/1974  Canada ........................... 424/273 R

OTHER PUBLICATIONS

Anon I, Chem. Abstracts, vol. 74, abst. 11066m, (1971).
Anon II, Chem. Abstracts, vol. 75, abst. 97100s, (1971).
Anon III, Chem. Abstracts, vol. 82, abst. 116020d, (1975).
Korolkovas et al., Chem. Abstracts, vol. 78, abst. 164031x, (1973).
Quinlan, Chem. Abstracts, vol. 82, abst. 175229b, (Abst. of Canadian Pat. No. 946,742 supra), 1975.
Polin, Chem. Abstracts, vol. 85, abst. 37250n, (1976).
Chemical Abstracts, 8th Collective Subject Index (1967-1971), p. 24333S, (1972).

Primary Examiner—Jane T. Fan
Attorney, Agent, or Firm—H. G. Jackson

[57] ABSTRACT

There are provided a palatable anthelmintic resinate composition having improved storage and handling characteristics comprising from 2% to 5% of a resinate N,N-dialkylpiperazine carboxamide, from 0% to 7% of a resinated styryl pyridinium compound, from 18% to 60% of dessicated liver, from 20 to 47% of dry whey, and from 1% to 10% of polyvinylpyriolidone, carboxypolymethylene or mixtures thereof, said percentages being all by weight, and a method for preparing the same.

5 Claims, No Drawings

DIETHYLCARBAMAZINE RESINATE AND STYRLPYRIDINIUM RESINATE-DIETHYLCARBAMAZINE RESINATE EDIBLE ANTHELMINTIC TABLETS FOR COMPANION ANIMALS

This application is a continuation-in-part of my copending application, Ser. No. 74,211, filed Sept. 10, 1979 now abandoned.

SUMMARY OF THE INVENTION

The present invention relates to palatable acidic resinate compositions which contain a styrylpyridinium compound and/or an N,N-dialkylpiperazine carboxamide and find utility as palatable anthelmintic compositions for the treatment of helminthiasis in companion animals.

Styrylpyridinium compounds and methods for their preparation are disclosed in U.S. Pat. Nos. 3,177,116 and 3,179,559 issued Apr. 6, 1965 and Apr. 20, 1965; respectively. These patents are incorporated herein by reference. Similarly, N,N-dialkylpiperazine carboxamides are disclosed in U.S. Pat. No. 2,467,895 issued Apr. 19, 1949. This patent is similarly incorporated herein by reference. The above-identified compounds are shown to be useful for combatting helminthiasis in domestic animals. They are said to be effective when administered by the oral route. Administration of both the N,N-dialkylpiperazine carboxamide and the styrylpyridinium halides, in the form of capsules, tablets and in the feed, is contemplated by the patentees. However, it has been found that the styrylpyridinium compounds and the N,N-dialkylpiperazine carboxamides are not readily acceptable (i.e. unpalatable) to companion animals when administered in a form in which the active compound is permitted to come in contact with the animals taste buds. Over the years, veterinarians have continually complained that the available tablets, pills or formulated compositions marketed for admixture of the styrylpyridinium halides with feeds is unsatisfactory and has resulted in the reluctance of the animals to ingest the medicated feed, tablets or pills. It would, therefore, be highly advantageous and most desirable if the above-named compounds could be rendered palatable without destroying their efficacy. Furthermore, it would be most advantageous if a palatable composition, containing a N,N-dialkylpiperazine carboxamide, alone or in combination with a styrylpyridinium compound such as 1-methyl-2-(p-chlorostyryl) pyridinium salt, could be prepared in the form of a chewable tablet, pill, granulated product or the like. It would also be advantageous if said tablets, pills or granular product would not beomce more friable with againg and/or when stored under conditions of elevated temperatures.

Heretofore, it has been sated that, "both olfaction and taste are involved in canine food preferences". Delineating olfactory medicated preferences can be accomplished by split plate evaluations. Actual consumption of an article is a function of combined odor and taste acceptability which is herein interperted as palatability.

It is, therefore, an object of this invention to provide palatable, therapeutically effective anthelmintic compositions having improved storage and handling stability and containing a N,N-dialkylpiperazine carboxamide alone or in combination with a styrylpyridinium compound.

It is also an object of the present invention to provide methods for preparing diethylcarbamazine and/or styrylpyridinium compositions which are palatable, stable when admixed with animal feed stuffs and have improved storage and handling characteristics.

The present invention accomplishes these objectives by the provision of novel resinates of N,N-dialkylpiperazine carboxamide compounds having the formula:

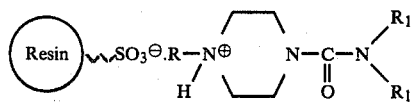

where R is hydrogen or $C_1$–$C_6$ alkyl and $R_1$ is alkyl $C_1$–$C_5$; and of styrylpyridinium compounds having the formula:

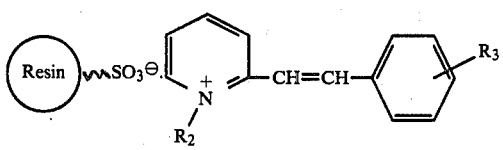

wherein $R_2$ is $C_1$–$C_4$ alkyl and $R_3$ is hydrogen or halogen; distributed in a composition consisting essentially of desiccated granular or powdered liver, Brewers yeast, dried whey and pharmaceutical grade polyvinyl pyrrolidone (PVP) having a mean molecular weight between about 30,000 and 40,000 such as PLASDONE K-29-32, K-26-28 or PLASDONE C, marketed by GAF Corporation, N.Y., N.Y., a pharmaceutical grade carboxypolymethylene (CPM) having an approximate molecular weight of 3,000,000 to 4,000,000 such as CARBOPOL 934 or 940 marketed by B. F. Goodrich Chemical Division, or mixtures of said polyvinyl pyrrolidone and carboxypolymethylene. Generally, it is preferred to employ about 1% to 10% and preferably about 1.75% to 5% by weight of PVP and/or CPM in the compositions of the invention.

While the above-mentioned carboxamide and styrylpyridinium compounds are described, respectively, in U.S. Pat. Nos. 2,467,895 issued Apr. 19, 1949 and 3,177,116 issued Apr. 6, 1965, no mention is made by the patentees of resinate forms of said compounds or of the improved palatability obtained with said forms.

The resinates of the above-identified compounds are prepared by reacting the free base or pharmacologically acceptable salt of the N,N-dialkylpiperazine carboxamide or the pharmacologically acceptable salt of the styrylpyridinium compound with an acidic cationic exchange resin under conditions whereby said compound becomes ionically bound to the acidic anion of the resin.

The diethylcarbamazine and/or the styrylpyridinium compound is bonded to the resin with sufficient ionic strength to withstand ionization in the mouths of animals. However, the efficacy of these anthelmintic agents is retained since the active compound is released from the resin in the stomach and/or intestinal tract of the animal ingesting the composition(s).

In the practice of the invention, palatable anthelmintic resinate tablets, exhibiting improved storage and handling characteristics, are prepared by admixing from 18% to 60% by weight of desiccated granular or powdered liver, but preferably granular liver; with 0% to 40% by weight of Brewers yeast; 20% to 47% by weight of dried whey, preferably spray dried; 1% to 10% by weight of polyvinylpyrrolidone, carboxypolymethylene or mixtures thereof; 2% to 5% by weight of diethylcarbamazine resinate and from 0 to 7% by weight of a styrylpyridinium resinate; said resin employed in the preparation of said resinates having a particle size of less than 800μ and preferably an average particle size between about 45μ and 300μ. Said ion exchange resin being further characterized as a strongly acidic high capacity sulfonic cation exchange resin preferably of the polystyrene divinylbenzene type having from 4 to 8% cross linkage.

Preferred compositions comprise about 3% by weight of diethylcarbamazine resinate; about 1.75% to 5.0% by weight of polyvinylpyrrolidone, carboxypolymethylene or mixtures thereof; 20% to 30% by weight of desiccated liver; 30% to 20% by weight of Brewers yeast and from 42% to 45.25% by weight of dry whey.

Preferred mixed drug compositions of the invention comprise about 3% by weight of diethylcarbamazine resinate; about 5% by weight of 1-methyl-2-(p-chlorostyryl)pyridinium resinate; about 5% by weight of polyvinylpyrrolidone, carboxypolymethylene or mixtures thereof; about 40% to 47% by weight of dried whey and about 40–47% by weight of desiccated liver and/or Brewers yeast, provided that at least 18% by weight of said composition is desiccated liver.

In the above-said compositions the resins used for the preparation of the diethylcarbamazine resinate and/or the styrylpyridinium resinate are high capacity sulfonic cationic exchange resins of the polystyrene divinylbenzene type with an average particle size preferably in the range of from 45μ to 300μ.

Preparation of the diethylcarbamazine resinate and styrylpyridinium resinate can be achieved by admixing the diethylcarbamazine compound with deionized water or the styrylpyridinium compound with an alcohol-deionized water mixture and intimately contacting the resulting mixture with a high capacity, sulfonic acid cationic exchange resin of a 4% to 8% divinylbenzene cross-linkage and a screen size of about 16 to 50 mesh. These resins generally have a loading capacity of about 4.5 to 5.0 milliequivalents per gram of dry resin. The thus prepared resinate is then separated from the supernatant liquid and washed repeatedly with deionized water until the wash water has a pH of about 4.5. The resin is then dried and ground or milled to a particle size of about 800μ and preferably to an average particle size between 45μ and 300μ. The resinates, thus prepared, can be used separately to formulate edible tables or they may be admixed to prepare edible tablets containing both compounds.

In the preparation of the above-mentioned resinates, alcohols such as methanol, ethanol, propanol, isopropanol, butanol, isobutanol, pentanol-1, or pentanol-2, may be employed.

Strongly acidic resins are preferred in the preparation of the resinates of this invention since they provide resinates in which the diethylcarbamazine and/or styrylpyridinium compounds are more strongly bonded to the ion exchange resin to substantialy prevent the compounds ionizing in the mouth of the animal to which they are fed. Among the preferred strongly acidic resins are sulfonated polystyrenes prepared from styrene and divinylbenzene which functions as a cross-linking agent. These resins include AMBERLITE ® IR-120, and DOWEX ® 50 and 50W. Sulfonated phenolic resins, may also be used and may include AMBERLITE ® IR-1; cellulose alkylsulfonic acid resins such as CELLEX SE resin and the like may also be utilized in the preparation of the resinates of this invention.

The reaction to form the resinates can be carried out over a wide temperature range so long as the solvent remains fluid and is not evaporated in excessive amounts. For example, the reactions can be conducted at a temperature between about 0° and 100° C. and preferably at about 20° to 50° C.

The diethylcarbamazine or styrylpyridinium solution can be contacted with the resin in any convenient manner such as by mixing the solution with the finely divided resin or by passing the solution of the anthelmintic agent through a resin bed. The molar ratio of anthelmintic agent to resin employed is not critical and is usually within the range of 0.125:1 to 3:1, preferably 0.5:1 to 2:1. A ratio within the preferred range permits efficient loading of the resin within a reasonable period of time. The anthelmintic resinates obtained in accordance with this invention contain about 10% to 60% by weight of anthelmintic and preferably about 40% to 55% of said anthelmintic. The resinate compositions can be prepared by either a batch or a continuous process and if desired both the diethylcarbamazine and styrylpyridinium compound may be loaded on a single resin. However, it is essential that in this arrangement the styrylpyridinium be loaded first and then the loaded resin thoroughly washed before the diethylcarbamazine is loaded on the resin. In this practice the resin is loaded only to about 25% to 33% by weight with the styrylpyridinium, determined or the basis of the dry weight of the resin, and then with about 13% to 18% by weight with diethylcarbamazine, determined on the basis of the dry weight of the resin. The preferred loading ratio of styrylpyridinium to diethylcarbamazine or sequentially loaded resins is about 1.67 to 1. However, ratios as low as 1.25 to 1 may be used.

The sequentialy loaded resinate, containing both the N,N-dialkylpiperazine carboxamide and the styrylpyridinium compound, may be illustrated as follows:

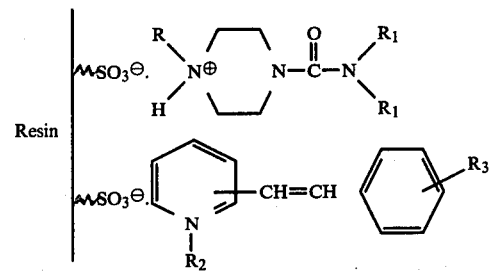

wherein R, R₁, R₂ and R₃ are as defined above.

I have found it feasible to load two cationic chemical substances sequentially onto the same cation exchange resin bead in its Hydrogen ion form, as illustrated below where A=Compound A, and B=Compound B:

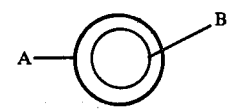

For this reaction sequence to occur Compound A must have a stronger affinity for the acid site on the resin than Compound B and no counterions can be present during the loading of Compound B as counterions would remove Compound A already loaded. This means that Compound B must be added as the base to prevent perturbation of Compound A. Compound A can be added as its acid salt but counterions formed must be removed by rinsing with distilled water before resin beads are exposed to the solution of Compound B.

In our specific application styrylpyridinium chloride (Styrid ®) as an aqueous methanol (25% by vol.) solution was first loaded onto Dowex 50W-X4, 50/100 mesh, Hydrogen Ion Form (AC3270-60). The resin beads were rinsed free of the hydrochloric acid formed with distilled water and then exposed to an aqueous solution of diethylcarbamazine base (Caricide ® base) and finally rinsed with distilled water. The beads were then dried to a water content of 1.4%. Chemical analysis revealed:

Styrid ®=25.585%
Caricide ® Base=16.49%

This actual Styrid to Caricide Base ratio of 1.55 conforms closely to the theoretical therapeutic drug ratio of 1.67 (i.e. 5/3) required.

This same process was repeated using a 47 micron mean particle size milled cation exchange resin available commercially from Ecodyne as Powdex and is said to be made from either Rohm and Haas' IR120 (20/50 mesh, 8% DVP, H+ Form) or Dowex 50W-X8, H+ Form, 20/50 mesh. The dry finely powdered end product assayed:

Styrid ®=24.2%
Caricide ® Base=15.4%

The Styrid to Caricide Base ratio is 1.57 compared to the theoretical ratio of 1.67.

The value of sequentially loaded ion exchange drug resinates lies in these areas:
1. Improved palatability as in tablets, suspensions and animal feeds.
2. Improve chemical stability in drug forms cited in (1) above.
3. Altered drug release pattern in the target species, as to provide a single dose containing two or more drugs released sequentially in the patient.

I have also found it possible to sequentially load caricide on a resin with an anthelmintically inactive component. In this preparation the anthelmintically inactive compound is loaded first onto the resin acid sites closest to the bead surface. An anthelmintically inactive safe component which can be used is cetylpyridinium chloride (a quaternary germicide currently commercially available in antiseptic throat lozenges) and is loaded onto only 1% to 10% of the total available acid sites, followed by removal of counterions formed by rinsing with distilled water, then loading diethylcarbamazine base onto the remaining available acid sites. The resin particle size should be as large as possible (to lower resin surface area to a minimum) while still providing acceptable content uniformity in the direct compression tablet granulation and in the finished tablet dosage form. This particle size limit lies in the 50 to 100 mesh particle size range corresponding to 150 to 300 micrometer particles. For Caricide 8% divinylbenzene cross-linkage would be preferred over the 4% level in the strong cation exchange resin since drug (i.e. Caricide) release would be slower.

Sequential loading of more than two active compounds can also be achieved with the process of the present invention.

It is conceivable that more than two active compounds can be loaded onto a single ion exchange resin bead. If three compounds with different affinities for the acid (exchange) sites on an ion exchange resin such that the affinity of Compound A>Compound B>Compound C, then Compound A could be loaded first either as the free base or its acid salt. When made free of counterions Compound A resinate beads could be exposed to a solution of the base form of Compound B to give Compound AB resinate. AB resinate could then be admixed with a solution of the base form of Compound C to yield ABC resinate as illustrated here:

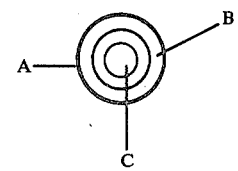

Also, if drug affinities for resin acid sites were such that Compound A>Compound B=Compound C, then A could be loaded first followed by a solution of B and C to give:

As previously suggested, the palatability of the compositions of the present invention, to companion animals, is achieved by the use of the active ingredients in resinated form and by the inclusion of from about 18% by weight, to 60% by weight, of desiccated liver alone or in combination with up to 40% by weight, of Brewer's yeast. The enhanced palatability of the compositions of the invention is demonstrated by the palatability studies reported below.

The improved storage and handling stability of the tableted compositions is achieved by inclusion in the compositions of the invention of from about 20% to 47% by weight, of whey, and 1% to 10% and preferably from 1.75% to 5.0% by weight, of polyvinylpyrrolidone, carboxypolymethylene or mixtures thereof.

The improved hardness of the tableted compositions stored under ambient conditions and/or at elevated temperatures is exemplified by the tablet hardness studies reported below.

Control of helminthiasis in companion animals, such as dogs, can be achieved by administering to said animals daily any number of tablets or parts of tablets according to body weight to provide appropriate anthelmintic activity, said tablets being prepared in accordance with method and compositions of the present invention. Generally from about 1 to 6 of a 2 gram tablet per day is preferred.

The following examples are provided for the purpose of illustrating the invention and are not intended to limit the scope thereof.

EXAMPLE 1

Preparation of Diethylcarbamazine Resinates and Styrylpyridinium Resinates

Diethylcarbamazine Resinate

Diethylcarbamazine (1125 kg real 5.653 kg mole) also named N,N-dimethyl-4-methyl-1-piperazinecarboxamide, is charged to 2240 liters of deionized water and agitated to dissolve it. To this solution is then added a high capacity sulfonic cation exchange resin of the polystyrene divinylbenzene type (2380 kg) AMBERLITE IR-120 ® manufactured by Rohm and Haas Co.. The reaction slurry is filtered, washed with deionized water (2240 liters), and dried at 80°–90° C. The dried deithylcarbamazine resinate (2380 kg) which assays 45.0% diethylcarbamazine free base is then milled to 30 mesh particle size.

The above-mentioned cation exchange resin has, before reaction, a density of 0.85 g/cc apparent, 1.26 g/cc true; water content 44–48%; exchange capacity of 4.40 milliequivalents/g dry and a screen size of from 16 to 50 mesh.

Styrylpyridinium Resinate

A 3960 gram quantity of a sulfonic acid-divinylbenzene resin (H+form) calculated to contain 1500 grams or 7.620 equivalents capacity of dry resin is mixed with a solution containing 2074 grams of 1-methyl-2-(p-chlorostyryl)-pyridinium chloride, 2000 ml of methanol and 3900 ml of deionized water. The mixture is diluted to 11,000 ml with deionized water and then allowed to settle and the supernatant liquid separated from the mixture by filtration. This washing treatment is repeated 10 times. The pH of the final wash is 4.50 and the pH of the deionized water is 4.85. The resinate is then dried at 75° C. for 48 hours and weighs 2,739 grams. The resinate passes through a 20 mesh screen and assays 52.38% 1-methyl-2-(p-chlorostyryl)-pyridinium as the chloride and has a KF moisture content of 1.305%. The resin employed in the above preparation is marketed under the tradename Powdex by the Graver Water Conditioning Co., N.Y., and is about 47$\mu$ material.

EXAMPLE 2

Preparation of Diethylcarbamazine Resinate

A mixture washed Powdex ® resin (1667 g wet resin, calculated to contain 698.0 g dry resin or 3.546 equivalents capacity) and 500 ml of deionized water are mixed in a vessel. To this mixture is added 719.28 g (706.6 g, real; 3.546 moles) of diethylcarbamazine base. The mixture is stirred for 4 hours and then filtered and washed repeatedly with deionized water. The resinate is collected and dried at 85° C. for 24 hours. The dried resinate weighs 1389 g and assays 50.59% and 50.30% diethylcarbamazine base. Following the procedure of Example 6 below, the styrylpyridinium can be sequentially loaded on to the diethylcarbamazine resinate.

EXAMPLE 3

Preparation of Diethylcarbamazine Resinate-Edible Tablets

Diethylcarbamazine resinate (71.28 kg 3.24% w/w) prepared in accordance with the procedure of Example 1 is blended with 1.10 kg of colloidal silicon dioxide. Brewers yeast 873.62 kg (39.71% w/w) is passed through a 30 mesh screen blended with the prepared diethylcarbamazine mixture. The resulting mixture is then admixed with 660.00 kg of microcrystalline cellulose. The mixture is passed through a 30 mesh screen, blended with 154.00 kg of stearic acid, 440.00 kg of dessiccated, granular, liver (20% w/w) and compacted into 2.20 g±2% tablets using a commercial tableting machine.

EXAMPLE 4

Preparation of Diethylcarbamazine Resinate-Edible Tablets

Diethylcarbamazine resinate (71.2 kg 3.24 w/w) prepared in accordance with example 3 is admixed with 0.44 kg of sodium aluminum silicate. Desiccated, powdered, liver (444.0 kg 20.0% w/w) is then passed through a 30 mesh screen and blended with the previously prepared resinate mixture and to this mixture is added 874.28 kg (34.94% w/w) of Brewers yeast, 660.00 kg of microcrystalline cellulose and 1540.00 kg of stearic acid. The thus prepared mixture is thoroughly blended and then formed into 2.20 g tablets using a commercial tableting machine.

EXAMPLE 5

Preparation of diethylcarbamazine resinate-styrylpyridinium resinate edible tablets Diethylcarbamazine resinate (71.28 kg 3.24% w/w) and 1-methyl-2-(p-chlorostyryl)-pyridinium resinate (104,94 kg 4.77% w/w) prepared in accordance with example 1 are blended with 1.1 kg of colloidal silicon dioxide. Desiccated-granular liver (440.0 kg 20.0% w/w) is screened through a 30 mesh screen and admixed with the resinate mixture. Brewers yeast (768.68 kg 34.94% w/w) is then passed through a 30 mesh screen and mixed with the previously prepared resinate mixture. Microcrystalline cellulose (660.00 kg) and 154.00 kg of stearic acid are blended with the above-noted mixture and the resulting formulation formed into 2.2 g tablets using a commercial tableting machine.

EXAMPLE 6

Sequentially Loaded Styrylpyridinium-Diethylcarbamazine Resin

DOWEX ® 50W, sulfonated polystyrene-divinylbenzene cross-linked acidic resin, 3000 g is placed in a 10 l. graduated cylinder. Styrylpyridinium chloride (510.5 g) is then dissolved in 1200 ml of deionized water and 300 ml of methanol and added to the DOWEX 50W resin. The mixture is stirred for 2 hours and then permitted to settle and the acidic supernatant liquid decanted. The remaining styrylpyridinium resinate is washed 3 times with deionized water, then permitted to settle and the supernatant liquid separated from the resinate Diethylcarbamazine base (306.3 g) is then added to the resinate and sufficient deionized water added to adjust the volume of the mixture to 11 l. The resulting mixture is stirred for 2 hours until the diethylcarbamazine is loaded on the resin along with the styrylpyridinium. The mixture is washed several times and until the final wash and resin mixture has a pH of 4.30. The supernatant liquid is separated from the styrylpyridiniumdiethylcarbamazine resinate which is then dried and ready for use in preparation of the edible tablets.

The above procedures are repeated using POWDEX Resin (IR 120 ground to an average particle diameter of 45$\mu$) (2820 g). The styrylpyridinium chloride (501. g) is the first drug to be loaded on the resin as described above. This is accomplished in a methanol water solution. The resin is washed 3 times with deionized water and the supernatant liquid decanted. Diethylcarbamazine (291. g) is then sequentially loaded onto the washed styrylpyridinium resinate and stirred for 17 hours. The mixture is permitted to settle, the supernatant liquid decanted and the remaining resinate washed with deionized water until the pH of the wash water mixture is about 4.6.

EXAMPLE 7

Preparation of Styrylpyridinium-Diethylcarbamazine edible tablets using sequentially loaded resin Styrylpyridinium-diethylcarbamazine sequentially loaded resinate (355.4 g) is admixed with 800 g of desiccated powdered liver, 1200 g of microcrystalline cellulose (AVICEL PH102); 1362. g of Brewers yeast; 2.0 g of silicon dioxide and 280. g of stearic acid. The composition, thus prepared, contained 8.885% by weight of the resinated drug, 20% by weight of liver, 30% by weight of microcrystalline cellulose, 34.065% by weight of the yeast, 0.05% by weight of the silicon dioxide and 7.0% by weight of the stearic acid.

The composition is compressed into chewable 2.2 g tablets having a Kilopond hardness rating of about 8.5 Kp. Substitution od dry whey for the microcrystalline cellulose and substitution of 2.5 to 5.0% PVP and 4.55 to 2.05% CPM for the stearic acid and silicon dioxide, in the above formulation, increases the hardness of the chewable tablets about 1 to 4 units on the Kp. scale.

EXAMPLE 8

Palatability Evaluation of Styrylpyridinium-Diethylcarbamazine edible tablets

The following tests are conducted to determine comparative acceptability of various formulations of tablets containing 1-methyl-2-(p-chlorostyryl)-pyridinium resinate and diethylcarbamazine resinate.

Twenty adult purebred Pointer-type dogs are used in these evaluations. The dogs are housed individually in outside pens. Each pen is 4 feet wide, 10 feet long and is provided with an attached shelter. Pointers are used for this test because of their organoleptic sensitivity to differences between products.

Each dog is tested for intestinal parasites by a flotation method using sodium nitrate solution and Fecasol ® kits. Dog 7 is found to have a slight infestation of *Toxascaris leonina* and Dog 12 a ruminant parasite. Both infestations are gone after 14 days.

Tests for Dirofilariasis are conducted using Knott's technique and all blood samples are free of microfilaria.

In the tests each dog is fed ad libitum a commerical dry dog food in self-feeders, and fresh, clean, water is available at all times.

A double choice format is employed with each dog being offered two choices of tables formulations simultaneously to determine acceptability preference.

The feed containers used are rectangular plywood sheets, 24 by 31 cm, 2 cm thick, with routed depressions, 3.7 cm in diameter and 1.1 cm deep.

Each dog is offered two tablets each morning and again late afternoon for five days. Tablet positions at presentation are altered each time by turning the containers 180° before placing it in the cage. Time of acceptance and which tablets is consumed first is noted for each offering. The container is left in the cage 30 minutes if the tablets are not readily consumed.

All dogs are less than 4 years of age and weigh between 35 and 52.5 pounds. The sex, habitus and initial and final weights of each dog are recorded and reported below. Also reported are the findings obtained in this test along with formulation used.

| English Pointers used in this test | | | | |
|---|---|---|---|---|
| Pen | Sex | Habitus | Initial weight lbs. | Final weight lbs. |
| 1 | F | muscular | 48 | 43 |
| 2 | F | light | 35 | 43 |
| 3 | F | light | 38 | 35.5 |
| 4 | F | muscular | 49 | 46 |
| 5 | F | light | 37 | 35.5 |
| 6 | F | fat | 49 | 47.5 |
| 7 | F | light | 39 | 39 |
| 8 | F | average | 41.5 | 43 |
| 9 | F | muscular | 46 | 42.5 |
| 10 | F | light | 40.5 | 40 |
| 11 | M | average | 45 | 42.5 |
| 12 | F | fat | 49.5 | 50 |
| 13 | M | muscular | 52 | 50 |
| 14 | F | light | 37 | 36 |
| 15 | M | muscular | 52.5 | 50.5 |
| 16 | F | average | 40 | 39 |
| 17 | M | muscular | 50 | 50.5 |
| 18 | F | light | 37 | 38.5 |
| 19 | F | average | 45 | 43 |
| 20 | F | light | 38 | 38.5 |

| First Preference Test Results For Styrylpyridinium-Diethylcarbamazine Resinate Tablets | | | | | | | | | | | |
|---|---|---|---|---|---|---|---|---|---|---|---|
| Comparisons: | A | B | B | C | A | D | B | E | F | G | G | H |
| Dog # 1 | 2 | 3 | 7 | 2 | 8 | 1 | 8 | 2 | 5 | 5 | 33 | 7 |
| 2 | 3 | 6 | 6 | 3 | 4 | 5 | 6 | 4 | 5 | 5 | 4 | 6 |
| 3 | 5 | 5 | 7 | 3 | 7 | 3 | 10 | 0 | 5 | 4 | 3 | 7 |
| 4 | 2 | 8 | 7 | 3 | 7 | 3 | 4 | 6 | 2 | 8 | 6 | 4 |
| 5 | 3 | 6 | 5 | 5 | 5 | 5 | 1 | 9 | 3 | 7 | 4 | 6 |
| 6 | 7 | 3 | 8 | 2 | 5 | 5 | 6 | 4 | 6 | 4 | 5 | 5 |
| 7 | 4 | 6 | 4 | 6 | 9 | 1 | 5 | 5 | 6 | 4 | 5 | 5 |
| 8 | 5 | 5 | 7 | 3 | 8 | 2 | 7 | 3 | 6 | 4 | 4 | 6 |
| 9 | 4 | 6 | 5 | 5 | 10 | 0 | 6 | 4 | 5 | 5 | 6 | 4 |
| 10 | 5 | 5 | 5 | 5 | 6 | 4 | 5 | 5 | 5 | 5 | 6 | 4 |
| 11 | 4 | 6 | 7 | 3 | 8 | 2 | 4 | 6 | 4 | 6 | 5 | 5 |
| 12 | 3 | 7 | 4 | 6 | 7 | 3 | 6 | 4 | 5 | 5 | 7 | 3 |
| 13 | 6 | 4 | 4 | 6 | 5 | 5 | 5 | 5 | 6 | 4 | 5 | 5 |
| 14 | 2 | 8 | 4 | 6 | 7 | 3 | 5 | 5 | 7 | 3 | 4 | 6 |
| 15 | 6 | 4 | 5 | 5 | 7 | 3 | 8 | 2 | 2 | 7 | 7 | 2 |
| 16 | 5 | 5 | 6 | 4 | 5 | 5 | 5 | 5 | 5 | 5 | 5 | 5 |
| 17 | 5 | 5 | 6 | 4 | 4 | 6 | 8 | 2 | 6 | 0 | 2 | 3 |
| 18 | 4 | 6 | 5 | 5 | 6 | 3 | 5 | 5 | 6 | 4 | 7 | 3 |
| 19 | 6 | 4 | 4 | 6 | 10 | 0 | 8 | 2 | 4 | 6 | 7 | 3 |

-continued

First Preference Test Results For
Styrylpyridinium-Diethylcarbamazine Resinate Tablets

| Comparisons: | A | B | B | C | A | D | B | E | F | G | G | H |
|---|---|---|---|---|---|---|---|---|---|---|---|---|
| | 20 | 4 | 6 | 6 | 4 | 9 | 1 | 6 | 4 | 6 | 4 | 3 | 7 |
| Totals: | 85 | 108 | 112 | 86 | 137 | 60 | 118 | 82 | 99 | 95 | 98 | 96 |
| Selected First) | | | | | | | | | | | | |

Tablet Compositions % w/w

A = 36.36% Desiccated liver
    18.18% Brewers yeast
    30.67% Microcrystalline cellulose
    2.92% Diethylcarbamazine resinate
    7.00% Stearic acid
    4.87% 1-methyl-2-(p-chlorostyryl)-pyridinium resinate
        Resinate particle size 300–800μ
    4% Sulfonic acid-divinylbenzene cross linkage B = 54.55% Desiccated liver
    30.66% Microcrystalline cellulose
    4.87% 1-methyl-2-(p-chlorostyryl)-pyridinium resinate
    2.92% Diethylcarbamazine resinate
    7.00% Stearic acid
        Resin particle size 300–800μ
    4% Sulfonic acid-divinylbenzene cross linkage C = 36.36% Brewers yeast
    18.18% Desiccated liver
    30.67% Microcrystalline cellulose
    4.87% 1-methy-2-(p-chlorostyryl)-pyridinium resinate
    29.2% Diethylcarbamazine resinate
    7.00% Stearic acid
        Resin particle size 300–800μ
    4% Sulfonic acid-divinylbenzene cross linkage D = Filarabits - Commercial edible formulation of Diethyl-carbamazine E = 36.36% Brewers yeast
    18.18% Desiccated powdered liver
    5.19% 1-methyl-2-(p-chlorostyryl)-pyridinium resinate
    3.01% Diethylcarbamazine resinate
    30.26% Microcrystalline cellulose
    7.00% Stearic acid
        Resin particle size 147–300μ,
    4% Sulfonic acid-divinylbenzene cross linkage F = 35.8% Brewers yeast
    18.0% Desiccated powdered liver
    5.97% 1-methyl-2-(p-chlorostyryl)-pyridinium resinate
    3.18% Diethylcarbamazine resinate
    0.05% Colloidial Silicon Dioxide
    30.00% Microcrystalline cellulose
    7.00% Stearic acid
        Resin particle size <147μ
    4% Sulfonic acid-divinylbenzene cross linkage G = 36.77% Brewers yeast
    18.0% Desiccated powdered liver
    5.28% 1-methyl-2-(p-chlorostyryl)-pyridinium resinate
    2.95% Diethylcarbamazine resinate
    30.00% Microcrystalline cellulose
    7.00% Stearic acid
        Resin particle size <147μ,
    8% Sulfonic acid-divinylbenzene cross linkage H = 36.52% Brewers yeast
    18.00% Desiccated powdered liver
    5.30% 1-methyl-2-(p-chlorostyryl)-pyridinium resinate
    3.18% Diethylcarbamazine resinate
    30.00% Microcrystalline cellulose
    7.00% Stearic acid
        Average resin particle size 45μ
    4% Sulfonic acid-divinylbenzene cross linkage From the above data it can be seen that formulation B, which contains approximately 55% by weight of liver, is most agressively accepted by dogs. Formulation A, containing approximately 18% by weight of Brewers yeast and 40% by weight of liver and formulations C and E, containing about 18% by weight of liver and 40% by weight of Brewers yeast are the next most palatable formulations to the dogs. All these formulations were more palatable than the commercial Filarabit (diethylcarbamazine) formulation.

Formulation F,G and H were all readily acceptable to the test dogs and were equivalent in palatability ratings. In all cases, most dogs ate both tablets as treats within 1 minute. The use of about 20% liver or more improves the rate of acceptance presumable by both beneficial olfactory and gustatory stimulation.

EXAMPLE 9

Palatability evaluation of styrylpyridinium-diethylcarbamazine edible tablets

The test described in example 8 above is repeated using 16 to 20 mongrel dogs weighing between 20 to 60 pounds each. Tablets A,B,C, and D, described in Example 8, are evaluated in this test along with three different formulations designated I,J and K. The latter formulations have the following compositions:

```
I =  18.18% Desiccated liver powder
     36.36% Brewers yeast
     30.10% Monocrystalline cellulose
      5.28% 1-methyl-2-(p-chlorostyryl)-pyridinium
            resinate (average resin size: 300–800μ, 4% cross linkage)
      3.08% Diethylcarbamazine citrate (no resin)
      7.00% Stearic acid
J =  46.36% Brewers yeast
      8.18% Desiccated liver powder
     30.49% Monocrystalline cellulose
      5.05% 1-methyl-2-(p-chlorostyryl)-pyridinium resinate
      2.92% Diethylcarbamazine resinate
      7.00% Stearic acid
K =  54.54% Brewers yeast
     30.49% Monocrystalline cellulose
      5.05% 1-methyl-2-(p-chlororstyryl)-pyridinium resinate
      2.92% Diethylcarbamazine resinate
      7.00% Stearic acid
```

As in example 8, the tablets are offered to each dog twice daily for five days. Preference for formulations is reported as % consumed first.

First Preference Test Results
Styrylpyridinium-Diethylcarbamazine Formulations

| Formulation | | % liver | % yeast | % consumed first |
|---|---|---|---|---|
| A | | 36.36 | 18.18 | 56.4 |
| C | | 18.18 | 36.36 | 43.6 |
| A | | 36.36 | 18.18 | 41.0 |
| B | | 54.55 | 0 | 59.0 |
| B | | 54.55 | 0 | 66.0 |
| D | (Filaribits) | — | — | 34.0 |
| C | | 18.18 | 36.36 | 67.0 |
| I = | Non-resinated Diethylcarbamazine and Styrylpyridinium resinate | 18.18 | 36.36 | 33.0 |
| J | | 8.18 | 46.36 | 56.0 |
| K | | 0 | 54.54 | 44.0 |

From the above data it can be seen that the formulation prepared with about 54.55% liver was the most preferred formulation. However, formulations A, B and C, were all acceptable and relatively preferred over the commercial "Filaribits" ® diethylcarbamazine formulation. Thus, it is apparent that styrylpyridinium resinate-diethylcarbamazine resinate formulations containing 20% to 60% by weight of liver and 0–40% by weight of yeast are more acceptable, i.e. palatable, to dogs than the presently offered commercial preparations. Additionally, formulation containing non-resinated diethylcarbamazine was not well accepted and the 0% liver formulation was less well received than the 8.18% liver formulation.

EXAMPLE 10

Palatability Evaluation of *Styrylpyridinium *Diethylcarbamazine edible tablets

Twenty-five to 29 privately-owned pet dogs representing a variety of ages, bodyweights, breeds and both sexes were used in a series of 3 day acceptance studies. STYRID CARICIDE Tablets to provide therepeutic levels of styrylpyridinium and diethylcarbamazine for a 20 lb. dog were formulated with a variety of liver contants and resinated or non resinated active drug components. For formulations used (A thur K) were specified in Examples 8 and 9. Each dog was presented the appropriate number of tablets according to body weight for three consecutive days. The percent acceptance for each formulation was calculated from the total number of daily dosages totally accepted as compared to the total number of tablet presentations.
*Styrulpyridinium=STYRID=1-methyl-2-(p-chlorostyryl)pyridinium
*Diethylcarbamazine=CARICIDE

| Formulation | % Liver | % Yeast | Drugs | Acceptance |
|---|---|---|---|---|
| A | 36.36 | 18.18 | CARICIDE Resinate STYRID Resinate | 96% |
| B | 54.55 | 0 | CARICIDE Resinate STYRID Resinate | 96% |
| C | 18.18 | 36.36 | CARICIDE Resinate STYRID Resinate | 96% |
| I | 18.18 | 36.36 | CARICIDE Citrate STYRID Resinate | 76% |
| J | 8.18 | 46.36 | CARICIDE Resinate STYRID Resinate | 80% |
| K | 0 | 54.54 | CARICIDE Resinate STYRID Resinate | 61% |

A definite preference for the resinate tablets containing from 18.18 to 54.55% liver relative to tablets containing 18.18% liver with non-resinated diethylcarbamazine. Additionally, formulations with 8.18% or less liver were relatively poorly accepted.

EXAMPLE 11

Hardness Evaluation of Diethylcarbamazine Resinate and Styrylpyridinium Resinate-Diethylcarbamazine Resinate tablets after storage for an extended time period at room temperature and/or at 37° C.

For the following evaluations edible tablets were prepared by blending diethylcarbamazine resinate and styrylpyridinium resinate, with (1) desiccated liver, Brewers yeast, spray dried whey, polyvinylpyrrolidone and/or carboxypolymethylene; or (2) with dessiccated liver, Brewers yeast, microcrystalline cellulose, stearic acid and optionally, silicon dioxide or sodium aluminum silicate.

The blended compositions were compressed into 2.2 gram chewable tablets using a commercial tableting machine operating at about 4.4 tons per square inch tableting pressure.

After the tablets were formed, they were placed on a Schleuniger tablet hardness tester and the hardness of said tablets determined. Values were determined on a scale of from 0 to 28 and reported as Kilopond (Kp) numerical values.

Compositions prepared and evaluated are described below.

To determine the effects of storage for extended periods of time tablets were stored at room temperature and/or at 37° C. for the desired period. After storage the tablets from the stored batches were placed on the hardness tester and the Kilopond hardness values determined.

| Chewable tablet Compositions Evaluated for Hardness for extended periods and/or at Elevated temperatures | | |
|---|---|---|
| | | % by weight |
| (1) | Styrylpyridinium resinate | 5.30 |
| | Diethylcarbamazine resinate | 3.18 |
| | Powdered liver (desiccated) | 18.00 |
| | Brewers yeast | 36.52 |
| | Microcrystalline cellulose | 30.00 |
| | Stearic acid | 7.00 |
| (2) | Styrylpyridinium resinate | 5.05 |
| | Diethylcarbamazine resinate | 2.92 |
| | Powdered liver (desiccated) | 18.18 |
| | Brewers yeast | 36.36 |
| | Microcrystalline cellulose | 30.49 |
| | Stearic acid | 7.0 |
| (3) | Diethylcarbamazine resinate | 3.07 |
| | Silicon dioxide | .02 |
| | Powdered liver (desiccated) | 20.0 |
| | Brewers yeast | 39.91 |
| | Microcrystalline cellulose | 30.0 |
| | Stearic acid | 7.0 |
| (4) | Diethylcarbamazine resinate | 3.24 |
| | Powdered liver (desiccated)-30 mesh | 20.0 |
| | Brewers yeast | 39.74 |
| | Microcrystalline cellulose | 30.0 |
| | Sodium aluminum silicate | 0.02 |
| | Stearic acid | 7.0 |
| (5) | Styrylpyridinium resinate | 5.19 |
| | Diethylcarbamazine resinate | 3.01 |
| | Brewers yeast | 36.36 |
| | Powdered liver (desiccated) | 18.18 |
| | Microcrystalline cellulose | 30.26 |
| | Stearic acid | 7.0 |
| (6) | Diethylcarbamazine resinate | 3.08 |
| | Carboxypolymethylene | 1.0 |
| | Brewers yeast | 30.0 |
| | Granular liver (desiccated)-18 mesh | 20.0 |
| | Spray dried whey-18 mesh | 45.92 |
| (7) | Diethylcarbamazine resinate | 3.08 |
| | Carboxypolymethylene | 1.75 |
| | Brewers yeast | 30.0 |
| | Granular liver | 20.0 |
| | Spray dried whey | 45.17 |
| (8) | Diethylcarbamazine resinate | 3.08 |
| | Carboxypolymethylene | 2.50 |
| | Brewers yeast | 30.0 |
| | Granular liver | 20.0 |
| | Spray dried whey | 44.42 |
| (9) | Styrylpyridinium-Diethylcarbamazine resinate (25.58%/16.49%) | 8.89 |
| | Powdered liver (desiccated) | 20.0 |
| | Microcrystalline cellulose | 30.0 |
| | Brewers yeast | 34.65 |
| | Silicon dioxide | 0.05 |

| Chewable tablet Compositions Evaluated for Hardness for extended periods and/or at Elevated temperatures | | |
|---|---|---|
| | | % by weight |
| | Stearic acid | 7.00 |
| (10) | Diethylcarbamazine resinate | 3.08 |
| | Carboxypolymethylene | 2.50 |
| | Brewers yeast | 44.42 |
| | Powdered liver (desiccated)-30 mesh | 20.00 |
| | Microcrystalline cellulose | 30.00 |
| (11) | Diethylcarbamazine resinate | 3.08 |
| | Polyvinylpyrrolidone | 5.0 |
| | Spray dried whey | 41.92 |
| | Granular liver (desiccated) | 20.0 |
| | Brewers yeast | 30.0 |
| (12) | Diethylcarbamazine resinate | 3.08 |
| | Carboxypolymethylene | 5.0 |
| | Spray dried whey | 41.92 |
| | Granular liver (desiccated) | 20.0 |
| | Brewers yeast | 30.0 |
| (13) | Diethylcarbamazine resinate | 3.08 |
| | Polyvinylpyrrolidone | 2.50 |
| | Carboxypolymethylene | 2.50 |
| | Spray dried whey | 41.92 |
| | Granular liver (desiccated) | 20.0 |
| | Brewers yeast | 30.0 |
| (14) | Diethylcarbamazine resinate-50 mesh | 3.08 |
| | Spray dried whey | 41.92 |
| | Granular liver (desiccated) | 20 |
| | Polyvinylpyrrolidone | 2.50 |
| | Carboxypolymethylene | 2.50 |
| | Brewers yeast | 30.0 |
| (15) | Diethylcarbamazine resinate-50 mesh | 3.08 |
| | Spray dried whey | 46.92 |
| | Granular liver | 20.0 |
| | Brewers yeast | 30.0 |
| (16) | Diethylcarbamazine resinate | 3.08 |
| | Carboxypolymethylene | 0.50 |
| | Brewers yeast | 30.0 |
| | Granular liver | 20.0 |
| | Spray dried whey | 46.42 |

TABLE I

| Kilopond Hardness Evaluation of Test Compositions | | | | | |
|---|---|---|---|---|---|
| Composition No. | Initial Hardness Kp # | Days Storage at Room Temp. | Hardness Avg. Kp # | Days Storage at 37° C. | Hardness Avg. Kp # |
| 1 | 5.3 | 197 | 3.1 | — | — |
| 2 | 6.7 | 169 | — | +70 | 5.78 |
| 3 | 5.5 | 38 | — | +70 | 4.8 |
| 4 | 5.5 | 38 | — | +70 | 3.5 |
| 5 | — | 169 | — | +70 | 5.9 |
| 6 | 11.42 | 42 | 10.82 | 42 | 9.66 |
| 7 | 13.64 | 42 | 11.62 | 42 | 11.48 |
| 8 | 15.3 | 42 | 12.65 | 42 | 13.08 |
| 9 | 8.4 | 200 | 5.55 | — | — |
| 10 | 13.28 | 39 | 12.14 | 39 | 9.37 |
| 11 | 8.67 | 44 | 8.02 | 44 | 11.98 |
| 12 | 15.09 | 44 | 13.92 | 44 | 14.12 |
| 13 | 12.72 | 44 | 12.18 | 44 | 17.48 |
| 14 | 12.9 | 44 | 13.84 | 44 | >20 |
| 15 | 9.1 | 44 | 8.32 | 44 | 8.12 |
| 16 | 9.92 | 42 | 8.78 | 42 | 7.94 |

From the above data it can be seen that edible tablets containing, in addition to the resinated anthelmintic(s) agent, the palatability enhancing agents: Brewer's yeast and powdered or granular liver; and the hardening agents: dried whey, polyvinylpyrrolidone, carboxypolymethylene or mixtures thereof, are harder when initially prepared and when aged at ambient or elevated temperatures, than are similar compositions that do not contain said polyvinylpyrolidone and/or carboxypolymethylene.

The data also show that tablets prepared from compositions containing 5%, by weight, of polyvinylpyrrolidone or a mixture of polyvinylpyrrolidone and carboxypolymethylene are harder when aged at elevated temperatures than said tablets are when initially formed. As such, these tablets have superior storage and handling characteristics.

As hereinabove noted, the tablets of the present invention are marketedly increased in hardness. Thus, the hardness of diethylcarbamazine resinate tablets or diethylcarbamazine resinate-styrylpyridinium resinate tablets is increased by admixing a mixture of 2% to 5% of diethylcarbamazine resinate, 0% to 7% of styrlpyridinium resinate, 18% to 60% of desiccated liver, 0% to 40% of Brewer's yeast, and 20% to 40% of dried whey and from 1% to 10% of an adjuvant selected from the group consisting of polyvinylpyrrolidone, carboxypolymethylene and mixtures thereof, and compressing said latter mixture to a Kilopond hardness value of from 10 to 16, said percentages being by weight.

I claim:

1. A palatable, anthelmintic resinate composition having improved storage and handling characteristics, comprising: about 3% by weight of diethylcarbamazine resinate; about 1.75 to 5.0% by weight of polyvinylpyrrolidone, carboxypolymethylene or mixtures thereof; 20% to 30% by weight of desiccated liver; 30% to 20% by weight of Brewers yeast and from 42% to 45.25% by weight of dried whey.

2. The palatable anthelmintic resinate composition having improved storage and handling characteristics comprising: about 8 to 10%, by weight, of a sequentially loaded styrylpyridinium-diethylcarbamazine resinate, containing 25% to 33% by weight, of the 1-methyl-2-(p-chlorostyryl)pyridinium compound and 13% to 18% of diethylcarbamazine, 20%, by weight, of desiccated liver, 30%, by weight, of dried whey, 35%, by weight, of Brewers yeast and from 5% to 7%, by weight of, polyvinylpyrrolidone, carboxypolymethylene or mixtures thereof.

3. A method for sequentially loading an N,N-dialkylpiperazinecarboxamide and 1-methyl-2-(p-chlorostyryl)pyridinium chloride onto the same cation exchange resin comprising the steps:
   (1) Treating said cationic exchange resin with up to 33% by weight, of the chemical compound having the strongest affinity for the acid sites on the resin;
   (2) Thoroughly washing the thus prepared partially loaded resinate to remove all counterions therefrom; and
   (3) Treating the washed, partially loaded resin with up to 18% by weight of the free base of the chemical compound having lesser affinity for the acid cites on the resin than the chemical compound initially loaded on said resin.

4. A method according to claim 3 wherein said resin is a high capacity sulfonic cationic exchange resin having a particle size of less than 800 m ; said initially loaded chemical compound is 1-methyl-2-(p-chlorostyryl)pyridinium chloride and is loaded on said resin in an amount between 25% and 33% by weight determined on the basis of the dry weight of the resin; said second chemical compound is N,N-dialkylpiperazine carboxamide and is loaded on the resin in an amount between 13% and 18% by weight, determined on the basis of the dry weight of the resin.

5. A method according to claim 4 wherein said resin is a polystyrene-divinylbenzene type.

* * * * *